United States Patent [19]
Aghili

[11] Patent Number: 4,698,081
[45] Date of Patent: Oct. 6, 1987

[54] PROCESS FOR SEPARATING HYDROCARBON GAS CONSTITUENTS UTILIZING A FRACTIONATOR

[75] Inventor: Hafez K. Aghili, Katy, Tex.

[73] Assignee: McDermott International, Inc., New Orleans, La.

[21] Appl. No.: 847,065

[22] Filed: Apr. 1, 1986

[51] Int. Cl.⁴ .............................................. F25J 3/02
[52] U.S. Cl. ............................................ 62/24; 62/32; 62/42
[58] Field of Search .................. 62/23, 24, 31, 32, 42

[56] References Cited

U.S. PATENT DOCUMENTS

| | | | |
|---|---|---|---|
| 3,398,543 | 8/1968 | Horton | 62/11 |
| 3,849,096 | 11/1974 | Kniel | 62/23 |
| 4,162,273 | 7/1979 | Skraba | 62/24 |
| 4,171,964 | 10/1979 | Campbell et al. | 62/24 |
| 4,235,613 | 11/1980 | Castoe et al. | 62/24 |
| 4,278,457 | 7/1981 | Campbell et al. | 62/24 |
| 4,368,061 | 1/1983 | Mestrallet et al. | 62/24 |
| 4,370,156 | 1/1983 | Goddin, Jr. et al. | 62/24 |
| 4,410,342 | 10/1983 | Horton | 62/23 |
| 4,453,958 | 1/1984 | Gulsby et al. | 62/28 |
| 4,464,190 | 8/1984 | Gulsby et al. | 62/24 |

Primary Examiner—Ronald C. Capossela
Attorney, Agent, or Firm—Robert J. Edwards; Michael L. Hoelter

[57] ABSTRACT

A process for separating the gas components contained in liquified natural gas wherein a small amount of heavier reflux liquid (propane, butane, pentane, iso-butane and iso-pentane) is recycled to the top of a demethanizer column. This alters its chemical equilibrium causing methane to vaporize in large quantities and to separate from the liquified feed stream. A fractionator receives the heavier demethanized liquid end product from the demethanizer column and through distillation separates the lighter ethanes and propanes from the heavier reflux liquid, a portion of the latter being recycled to the demethanizer column.

12 Claims, 4 Drawing Figures

PROCESS FOR SEPARATING HYDROCARBON GAS CONSTITUENTS UTILIZING A FRACTIONATOR

FIELD OF THE INVENTION

This invention pertains to a method of separating hydrocarbon gas constituents such as methane, ethane, and propane in natural gas and more particularly to a method by which such separation is achieved in a controlled environment to affect the composition of product streams based on the economics of natural gas constituents.

BACKGROUND OF THE INVENTION

The history of separating gas constituents from natural gas is a relatively recent one. In the 1940's the first prototype natural gas cyrogenic turboexpander was built and in the 50's this turboexpander concept was applied to air plants, hydrogen plants, and helium purification plants. However, it wasn't until the 1960's that the first commercial natural gas turboexpander plant started operation. As commercial demand for these separated gases increased, many other such plants came into existence each with better and improved designs for separating the lighter elements (methane, ethane, and propane) from the heavier elements (butane, pentane and their iso-components) contained in natural gas.

Many patents exist pertaining to these improvements with some of the more relevant patents being those to Gulsby (U.S. Pat. Nos. 4,464,190 and 4,453,958), Horton (U.S. Pat. Nos. 4,410,342 and 3,398,543), and Campbell, et al. (4,278,457 and 4,171,964). While each of these patents are improvements over their predecessors, none of them address the commercial need for nearly 100% gas separation and recovery.

It is an object of this invention to provide a method of achieving controlled separation of the natural gas feed stream constituents. It is another object of this invention to utilize a distillation column and recycled streams from other parts of the plant to affect the chemical equilibrium in the top section of the column for most economical product recovery. Another object of this invention is to employ a return condensate line feeding a demethanizer column to more favorably alter the chemical equilibrium in this demethanizer column.

SUMMARY OF THE INVENTION

In accordance with this invention a demethanizing column in conjunction with reboilers, compressors, and turboexpanders separate the heavier liquid elements in the natural gas feed stream from the lighter vapor methane. This heavier liquid end product exits the bottom of demethanizer column where it enters a fractionator or distillation column. In the fractionator the lighter ethane and propane vapors are separated from the heavier liquid butanes, pentanes and their iso-components. A small portion of the heavier liquid end product from the fractionator, nearly all butane, pentane, iso-butane and isopentane, is recycled as reflux to the top of the demethanizer column. This additional amount of the heavier liquids in the demethanizer column alters the chemical equilibrium existing in this upper region of the demethanizer where the elements are predominantly all lighter vaporized gases. This reflux addition and the resulting change in equilibrium causes nearly 100% gas separation of the methane in the demethanizer thereby providing a pure demethanized end product while only sacrificing a small volume of the heavier liquids to achieve this result.

DETAILED DESCRIPTION OF THE INVENTION

Figure 1:
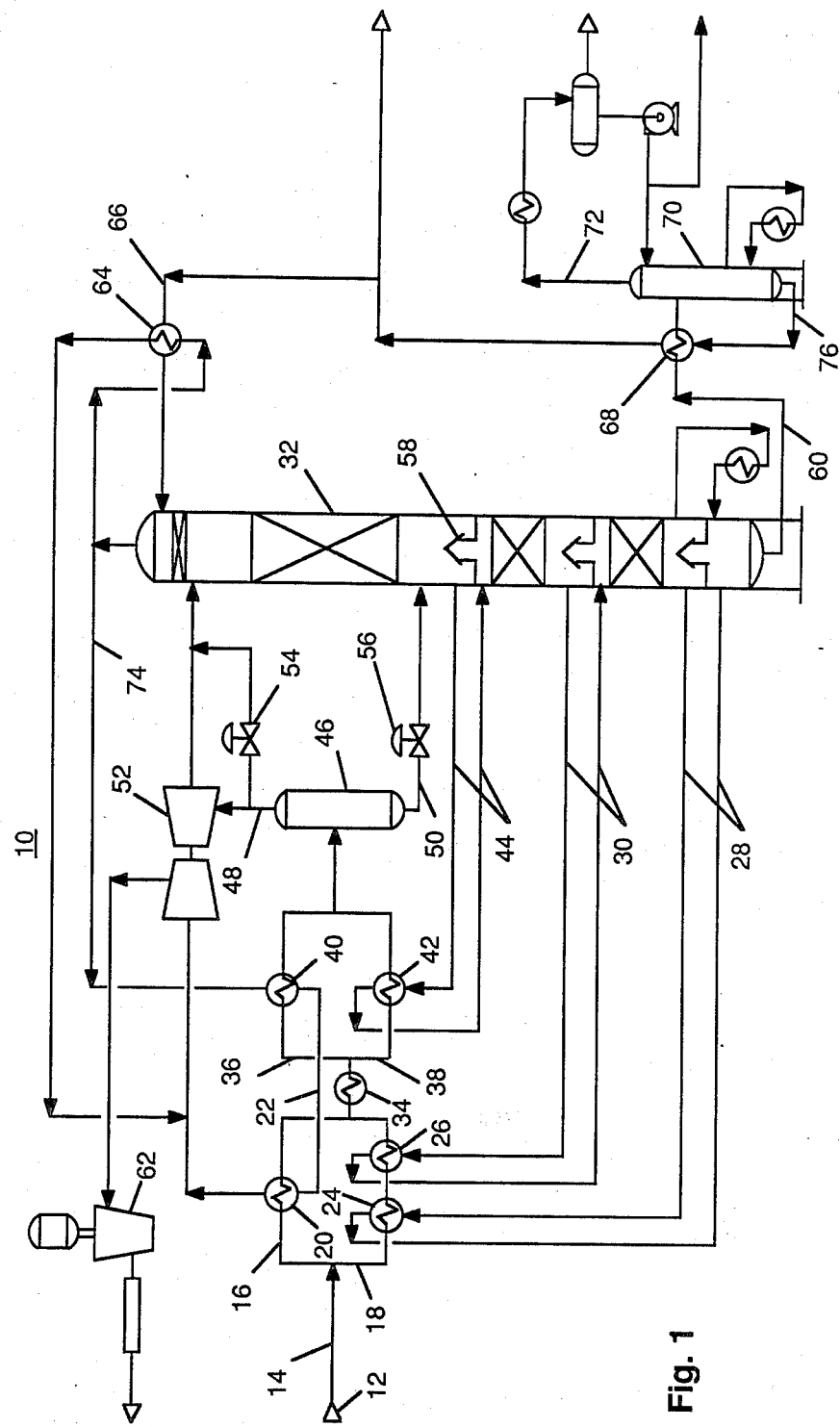
FIG. 1 is a schematic illustration of the operation of the demethanizer, fractionator, and return flux line.

Referring to FIG. 1, natural gas enters gas separator process 10 through inlet 12 after having first been dehydrated. This gas in line 14 is then divided into two separate streams 16 and 18 respectively. Gas stream 16 is cooled in warm gas/gas exchanger 20 by cool residue gas in line 22. Gas stream 18 is cooled in reboiler 24 and lower side heater 26 through which demethanizer liquid flows via lines 28 and 30 from demethanizer column 32.

From these exchangers, cooled gas streams 16 and 18 recombine and enter gas chiller 34 where this combined stream is further cooled by a refrigerant. After chiller 34, this chilled stream is again separated into two streams 36 and 38 for more cooling. Gas stream 36 is cooled in cold gas/gas exchanger 40 by cold residue gas directly from the top of demethanizer column 32. This residue gas is generally at a temperature of −140° F. As shown, this cold residue gas passes first through cold gas/gas exchanger 40 before traveling through warm gas/gas exchanger 20 via line 22. Gas stream 38 is cooled in upper side heater 42 by demethanized liquid flowing through line 44 from demethanizer column 32. This demethanizer liquid is generally at a temperature of −125° F. Cold gas streams 36 and 38 then recombine and enter high pressure separator 46 where the cooled inlet gas is separated into gas stream 48 and liquid stream 50. Gas stream 48, which by this time consists predominantly of the lighter methanes, ethanes, and propanes, is expanded to reduce its pressure such as by main expander 52 or across expansion valve 54. This expansion further cools the gas before it is fed into an upper region of demethanizer column 32. The condensed liquid stream 50 from high pressure separator 46 is also expanded, thereby reducing its pressure, such as across expansion valve 56, before entering the side of demethanizer column 32. By this time, liquid stream 50 consists predominantly of the heavier butanes, pentanes, and their iso-components.

As liquid is fed to demethanizer column 32, it flows downward under the force of gravity. During its journey, this liquid is engaged by rising vapors which strip the methane from this liquid as it passes through trays 58 in demethanizer column 32. This stripping operation produces a demethanized end product which is removed from the bottom of demethanizer column 32 via line 60. These rising methane vapors are generated from the heat obtained from heat exchangers 24, 26 and 42 via lines 28, 30 and 44.

A portion of the residue from the top of demethanizer column 32, where its temperature is approximately −140° F., is conveyed to cold gas/gas exchanger 40 and warm, gas/gas exchanger 20. This cold residue cools the incoming gas streams 36 and 16. From these heat exchangers, the warmed residue is compressed by the compressor side of main expander 52 and then by turbo recompressor 62 after which it is cooled and transported elsewhere. The remaining portion of the cold residue from the top of demethanizer column 32 passes through heat exchanger 64 which chills the recycled absorption stream in feed line 66 that is recycled to the top of demethanizer column 32.

Line 60 which exits the bottom of demethanizer column 32 transports the demethanized end product from column 32 to heat exchanger 68 which heats this product before it enters fractionator 70. Fractionator 70 acts as a distillation column or deethanizer and separates the lighter ethane component in this end product from the heavier propane, butanes, pentanes, and their iso-component. The overhead product from fractionator 70 exits through line 72 and this line contains essentially 100% of the ethane. Lower line 76, connected to the bottom of fractionator 70, transports the deethanized product from fractionator 70 through exchanger 68 where this deethanized end product heats the incoming demethanized end product in line 60. This deethanized end product from fractionator 70 is then recycled to the top of demethanizer column 32 via line 66. The addition of this portion of the heavier deethanized product to demethanizer column 32 alters significantly the chemical equilibrium in the top of column 32. This causes the lighter vaporized ethane in the top of this column to become liquid and fall to the bottom of column 32 while a small amount of propane and heavier constituents are vaporized to make up the dew point in stream 74. Feed line 66 acts as an absorption medium which enhances the recovery of ethane at the expense of a small reduction in the recovery of propane and heavier components.

Figure 2:
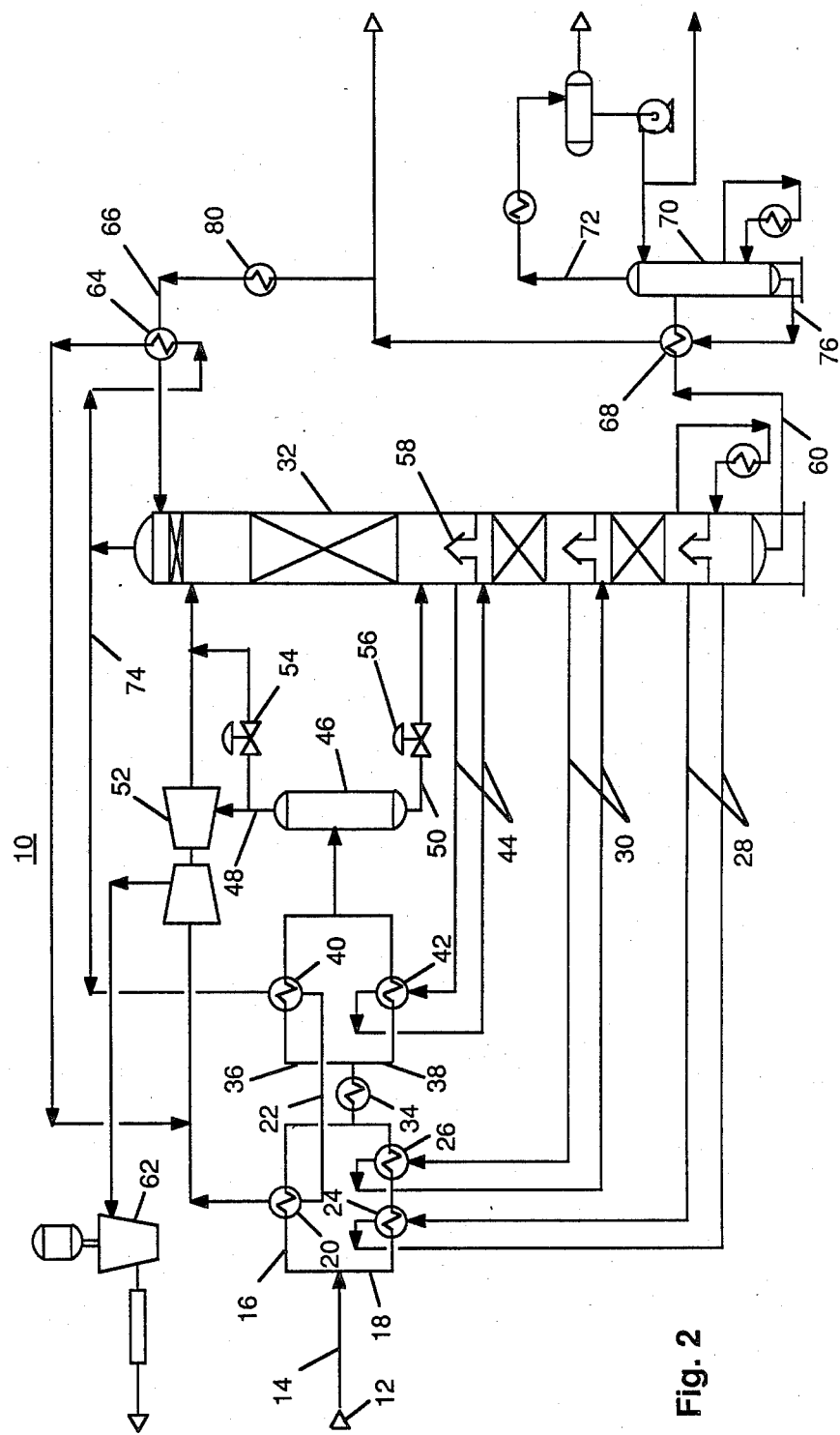
FIG. 2 is an alternate schematic illustration wherein the demethanized recycled absorption stream from the fractionator is initially cooled by a chiller and then a heat exchanger.

Another arrangement for the heat exchange of the recycled absorption in feed line 66 is shown in FIG. 2. In this case, the recycled absorption feed line 66 is first cooled via heat exchange in chiller 80 and then is further cooled in exchange 64 by a portion of the residue gas from demethanizer column 32.

Figure 3:
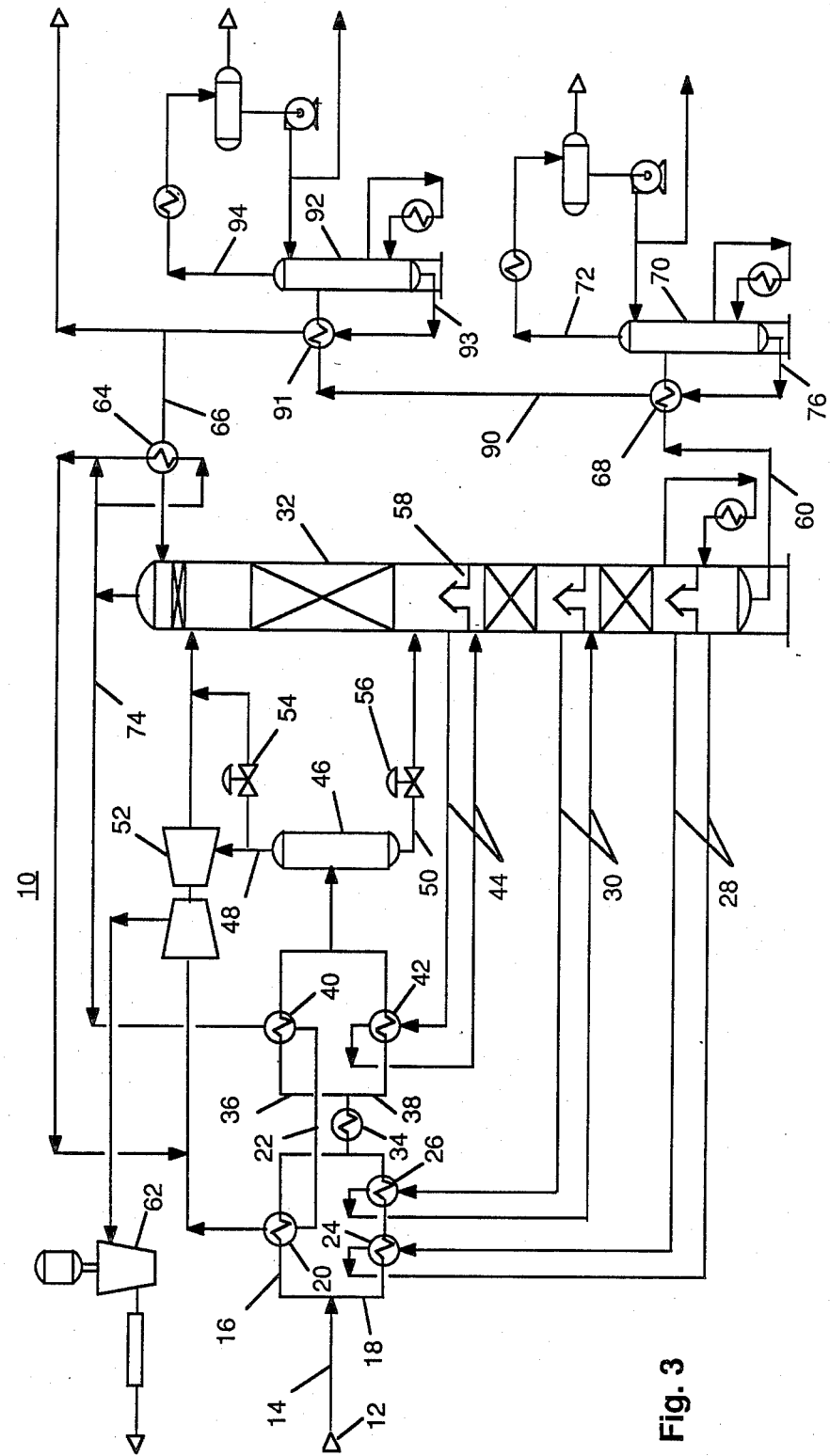
FIG. 3 is a further schematic illustration showing a deethanizer fractionator and a depropanizer fractionator.

FIG. 3 illustrates another variation of this process which uses a depropanized product stream as the absorption medium for demethanizer column 32. In this case, the bottom deethanized product from fractionator 70 flowing through line 90 is heated in heat exchanger 91 before entering depropanizer or fractionator 92. Fractionator 92 separates this incoming deethanized product into a top product that is predominantly propane and which leaves fractionator 92 via line 94, and a bottom product that consists of butanes and the heavier constituents and which leave fractionator 92 via line 93. A portion of this heavier depropanized product in line 93 is diverted to line 66 where it is cooled in heat exchanger 64 by the residue gases from demethanizer 32 before entering the top of demethanizer 32. This action causes the lighter vaporized ethane and propane in the top of column 32 to become liquid and fall to the bottom while a small amount of butane and heavier constituent are vaporized to make up the dew point in stream 74.

Figure 4:
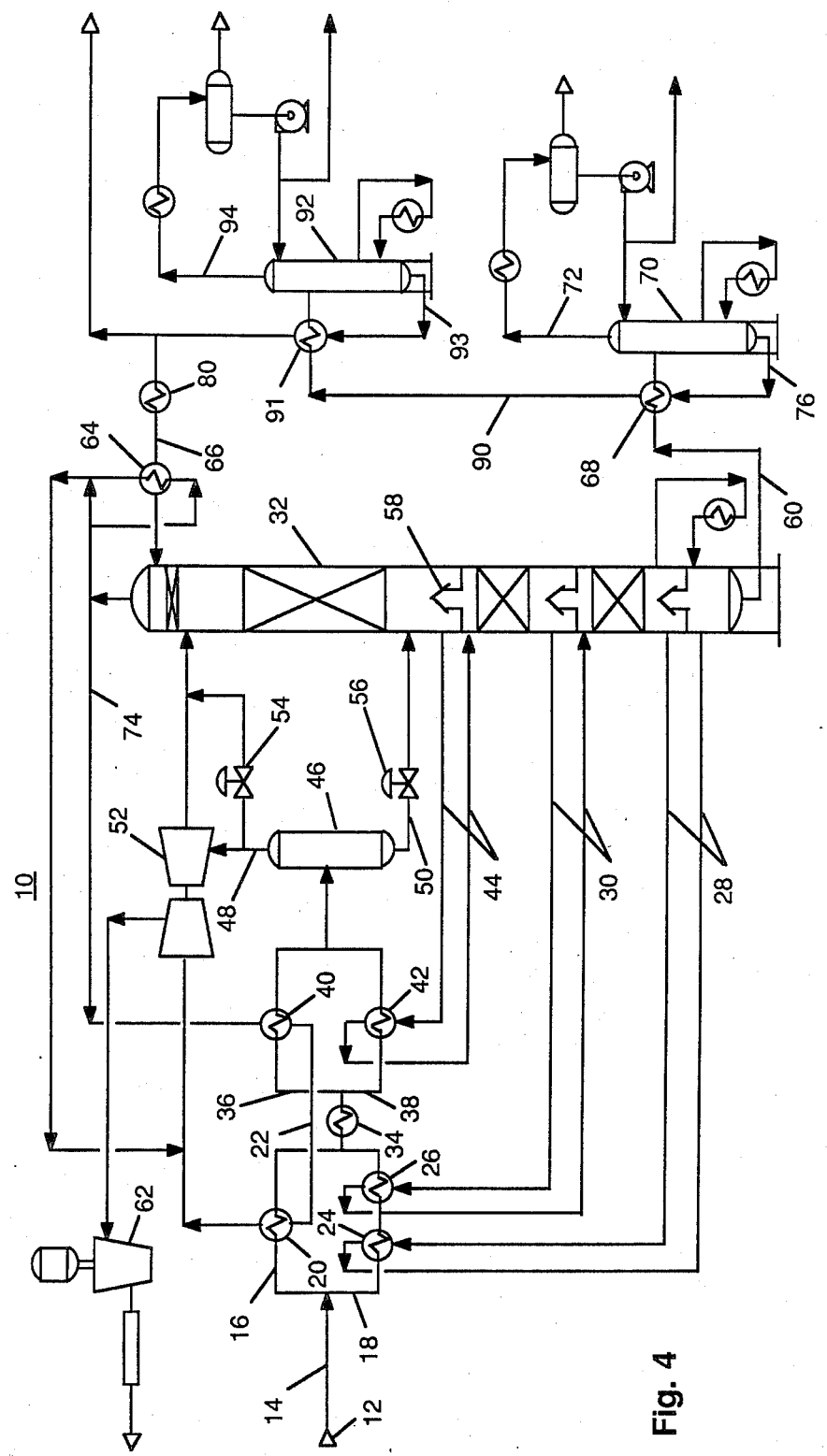
FIG. 4 is a schematic illustration similar to FIG. 3 but wherein the recycled depropanized product stream is initially cooled by a chiller and then a heat exchanger.

Another arrangement of the recycle absorption medium is shown in FIG. 4. In this case, the recycle absorption stream 66 is first cooled by heat exchange in chiller 80 with a refrigerant and then is further cooled in heat exchanger 64 by heat exchange with a portion of the residue gas from column 32.

What is claimed is:

1. A process for separating the constituents of a gas stream comprising:
    (a) lowering the temperature of said gas stream;
    (b) supplying said lower temperature gas stream to a high pressure separator, said high pressure separator separating said gas stream into predominantly vapor and predominantly fluid streams;
    (c) lowering the pressure of said predominantly vapor stream;
    (d) supplying said lower pressure vapor stream to an upper region of a demethanizer column;
    (e) lowering the pressure of said predominantly fluid stream;
    (f) supplying said lower pressure fluid stream to said demethanizer column at an elevation below said vapor stream;
    (g) removing cold vapor residue gas from an upper region of said demethanizer column, said vapor residue gas comprising predominantly of methane and other residual light vapors;
    (h) passing said vapor residue gas through at least one heat exchanger to raise the temperature of said vapor residue gas;
    (i) compressing said vapor residue gas for delivery elsewhere;
    (j) removing a cold demethanized product from a lower region of said demethanizer column;
    (k) supplying at least a portion of said demethanized product to a fractionator wherein said fractionator operates as a distillation column;
    (l) separating said demethanized product into an ethane overhead product and a deethanized bottom product;
    (m) removing a generally liquid deethanized product from a lower region of said fractionator;
    (n) drawing off a portion of said deethanized product;
    (o) lowering the temperature of said drawn off product; and,
    (p) supplying said lower temperature deethanized product to the top of said demethanizer column whereby the addition of said product alters the chemical equilibrium existing in the top of said demethanizer column thereby enhancing the recovery of ethane constituents at the expense of a small reduction in recovery of propane and heavier constituents.

2. A process as set forth in claim 1 wherein the temperature of said gas stream is lowered by separating said stream into at least two streams and cooling said streams in gas heat exchangers.

3. A process as set forth in claim 2 wherein at least one said gas heat exchanger uses said cold vapor residue gas as a refrigerant and another said gas heat exchanger uses said cold demethanized product as a refrigerant.

4. A process as set forth in claim 3 wherein the pressure of said predominantly vapor stream is lowered across expansion means.

5. The process as set forth in claim 4 wherein said expansion means comprise a main expander.

6. A process as set forth in claim 4 wherein said expansion means comprises an in-line expansion valve.

7. A process as set forth in claim 4 wherein the pressure of said predominantly fluid stream is lowered across an in-line expansion valve.

8. A process as set forth in claim 7 wherein said vapor residue gas is compressed on the compressor side of an expander.

9. A process as set forth in claim 8 wherein the temperature of said removed demethanized product is increased in a heat exchanger using said deethanized product as a heat exchange medium.

10. A process as set forth in claim 9 further comprising the step of supplying at least a portion of said deethanized bottom product to a second fractionator wherein said second fractionator separates said deethanized product into a propane overhead product and a depropanized bottom product.

11. A process as set forth in claim 10 wherein said depropanized bottom product from said second fractionator is cross exchanged with said deethanized bottom product feed to said second fractonator.

12. A process as set forth in claim 11 wherein a portion of said depropanized bottom product is cooled and supplied to the top of said demethanizer column wherein the addition of said product enhances the recovery of ethane and propane constituents in said demethanizer.

* * * * *